United States Patent [19]

Harkness

[11] Patent Number: Plant 6,953

[45] Date of Patent: Jul. 25, 1989

[54] HYBRID FLORIBUNDA ROSE PLANT

[75] Inventor: John L. Harkness, Suffolk, England

[73] Assignee: Weeks Wholesale Rose Grower, Inc., Ontario, Calif.

[21] Appl. No.: 214,023

[22] Filed: Jun. 29, 1988

[51] Int. Cl.[4] ..... A01H 5/00

[52] U.S. Cl. ..... Plt./24

[58] Field of Search ..... Plt./24

*Primary Examiner*—R. E. Bagwill

*Attorney, Agent, or Firm*—Foley & Lardner, Schwartz, Jeffery, Schwaab, Mack, Blumenthal & Evans

[57] ABSTRACT

A new Hybrid Floribunda rose for garden decoration, having as its seed parent, Judy Garland (cv. Harking), and as its pollen parent, Anne Harkness (cv. Harkaramel), characterized by large, upright clusters of buttercup yellow colored flowers that are long lasting and hold color well.

1 Drawing Sheet

This invention relates to a new and distinct variety of Hybrid Floribunda Rose. The plant is a bushy upright seedling suitable for garden decoration. It was bred in Hitchin, Hertfordshire, England, and has its seed parent Judy Garland (cv. Harking) and as its pollen parent Anne Harkness (cv. Harkaramel). The varietal denomination of the new variety is "Hartanna".

The new variety may be distinguished from other presently available commercial rose cultivars by the following combination of characteristics: its large upright clusters of long lasting flowers, its yellow bloom color essentially as described and illustrated herein, which lasts and holds well though the life of the flower and its vigorous disease resistant plant.

Asexual propagation by budding of the new variety as performed in Kern County, Calif., shows that the foregoing and other distinguishing characteristics true to perform and are established and transmitted through succeeding propagations.

The new rose may be distinguished from its seed parent, Judy Garland (cv. Harking), by the following combination of characteristics: whereas the new cultivar bears flowers of a yellow color substantially as described and illustrated herein, Judy Garland bears flowers that begin yellow and blush to red tones with aging. Hartanna has dark green foliage with a matte finish, whereas Judy Garland has bright green foliage with a semi-glossy finish. Harking bears flowers with 30 to 35 petals, whereas Hartanna bears flowers with lower petalage (25 to 28).

The new variety may be distinguished from its pollen parent, Anne Harkness (cv. Harkaramel) by the following combination of characteristics: whereas the new cultivar bears flowers of a yellow coloration substantially as described and illustrated herein, Anne Harkness bears flowers of an even apricot color. Harkaramel produces globular buds, whereas Hartanna produces more pointed to ovoid buds.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "9A" is plate 9A of The Royal Horticultural Society Colour Chart.

Parentage: Seedling.

*Seed parent.*—"Judy Garland".

*Pollen parent.*—"Anne Harkness".

Class: Hybrid Floribunda.

Descriptive matter which follows pertains to roses of the new cultivar grown outdoors in May 1988 in San Bernardino County, Calif. and is believed to apply to plants of the variety grown elsewhere in similar conditions of soil and climate.

FLOWER

The new variety bears its flowers sometimes singly, usually five or more per stem. Flowers are borne in regular rounded to pyramidal clusters on normal medium to long stems for the class. Outdoors, the plant blooms very abundantly and nearly continuously during the growing season. The flowers have a slight fruity fragrance.

BUD

The peduncle is of average length for the class, of average caliper, and usually stiff. It is moderately rough, with many stipitate glands, and few hairs. Peduncle color is between Yellow-green 152B and Yellow-green 144B.

Before the calyx breaks, the bud is of medium size for the class, moderately short to medium length, and pointed to avoid in shape. The surface of the bud bears few foliaceous appendages and stipitate glands, usually with slender foliaceous parts extending beyond the tip of the bud equal to one-half or more of its length. Before sepals fall, bud color is between Yellow-green 144A to B and Green 139B.

The inner surface of the sepals is covered with fine wooly tomentum; sepal margins are lined with some stipitate glands and hairs.

As the first petals open, the bud is small to medium for the class, medium length, and moderately pointed to ovoid in form. The color of the outside and inside surfaces of the newly opened petals is between Yellow 13B and Yellow 12A. The bud opens well and is not prevented from opening by wet cold, hot or dry weather.

BLOOM

When fully open, the bloom is somewhat medium size for the class, ranging from 8 to 10 cms. in diameter. Petalage is double with 25 to 28 petals and 4 to 8 petaloids arranged regularly. When partially open, the bloom form is somewhat cupped to globular, and the petals are somewhat loosely cupped to undulated with petal edges somewhat reflexed outward. When fully open, the bloom form is more cupped to full, and the petals are more loosely cupped to undulated.

As petals unfurl, flower coloring tends toward near buttercup yellow 15A to 15B where petals bunch which is closest coloring of the upper surface of inner petals. Outer petals are lighter toned near 15D to 13D on upper surface and similar coloring on petals undersurface. In open blooms, darker yellow centers are seen as yellow-orange coloring of reproductive organs become visible.

PETALS

The petals are of crisp substance and of moderate thickness, with inside surfaces slightly shiny to satiny and outside surfaces slightly shiny. The outside petals are nearly round to broadly ovate in shape with apices moderately rounded. The inside petals are broadly ovate to obovate in shape with apices moderately rounded.

MALE REPRODUCTIVE ORGANS

Stamens are average in number and are arranged regularly about the pistil; a few are mixed with petaloids. The filaments are of moderately short to medium length, most with anthers. The anthers are medium size for the class and all open approximately at the same times. Anther color is near Yellow 13A when immature and near Yellow-orange 21A at maturity. Pollen is moderate to abundant and near Yellow-orange 15B in color.

FEMALE REPRODUCTIVE ORGANS

Pistils are average to many in number (approximately 70). The styles are moderately uneven, short to average in length, somewhat thin to average in caliper, and very loosely bunched. Stigma color is near Yellow 11B. Ovaries are usually all enclosed in the calyx.

Hips on this variety when grown in Upland, California are short to average in length, very ovoid to globular in form, and near Yellow-orange 23A in color. The hip surface is moderately smooth with somewhat thick fleshy walls. The sepals are persistent, somewhat short to medium in length, and moderately spear-shaped. Seeds are average in number (approximately 12 to 18), and usually somewhat small to medium in size.

FOLIAGE

The compound leaves are usually comprised of three to five leaflets and are borne in moderate to normal quantities. The leaves are moderately small to medium size for the class, moderately heavy to crisp in texture, and somewhat semi-glossy to matte in finish. The leaflets are shaped very oval with moderately acute to mucronate apices and somewhat round bases. Their margins are usually simply serrate.

The upper surface of the mature leaf is between Green 137A and Yellow-green 147A. The under surface of the mature leaf is between Green 138B and Yellow-green 148B. The upper surface of the young leaf is between Green 137A and Yellow-green 147A, sometimes lightly suffused with near Greyed-red 178A. The under surface of the young leaf is between Green 138B and Yellow-green 148B, sometimes lightly suffused with near Greyed-red 178A.

The rachis is average in caliper and moderately grooved with some stipitate glands on the edges of the grooves. The under side of the rachis is very smooth.

The stipules are moderately long and of medium width with medium to long points that usually turn out at an angle of more than 45 degrees.

The plant displays an above average degree of resistance to powdery mildew and blackspot and rust as compared to other commercial varieties grown under comparable conditions in Upland, Calif.

GROWTH

The plant is bushy upright medium height to tall habit with moderately full branching. It displays very vigorous growth and the canes are of medium to heavy caliper for the class.

The major stems are between Greyed-green 191B and Yellow-green 148C. They bear few large prickles which are moderately long for the class. The large prickles are almost straight hooked slightly downward with a medium length somewhat narrow base; prickle color is near Greyed-orange 165B. The major stem bears no small prickles and no hairs.

The branches are between Yellow-green 144A and Green 137D. They bear few large prickles which are moderately long for the class. The large prickles are almost straight, hooked slightly downward with a medium length and somewhat narrow base; prickle color is near Greyed-orange 163C. The branches bear no small prickles and no hairs.

The new shoots are between Yellow-green 144A and Green 137B often suffused with near Greyed-red 178A. They bear few large prickles which are moderately long for the class. The large prickles are almost straight, hooked slightly downward with a medium length base; prickle color is near Greyed-red 178C. The shoots bear no small prickles and no hairs.

I claim:

1. A new and distinct variety of Hybrid Floribunda rose plant cv. Hartanna, and the parts thereof, substantially as described and illustrated herein.

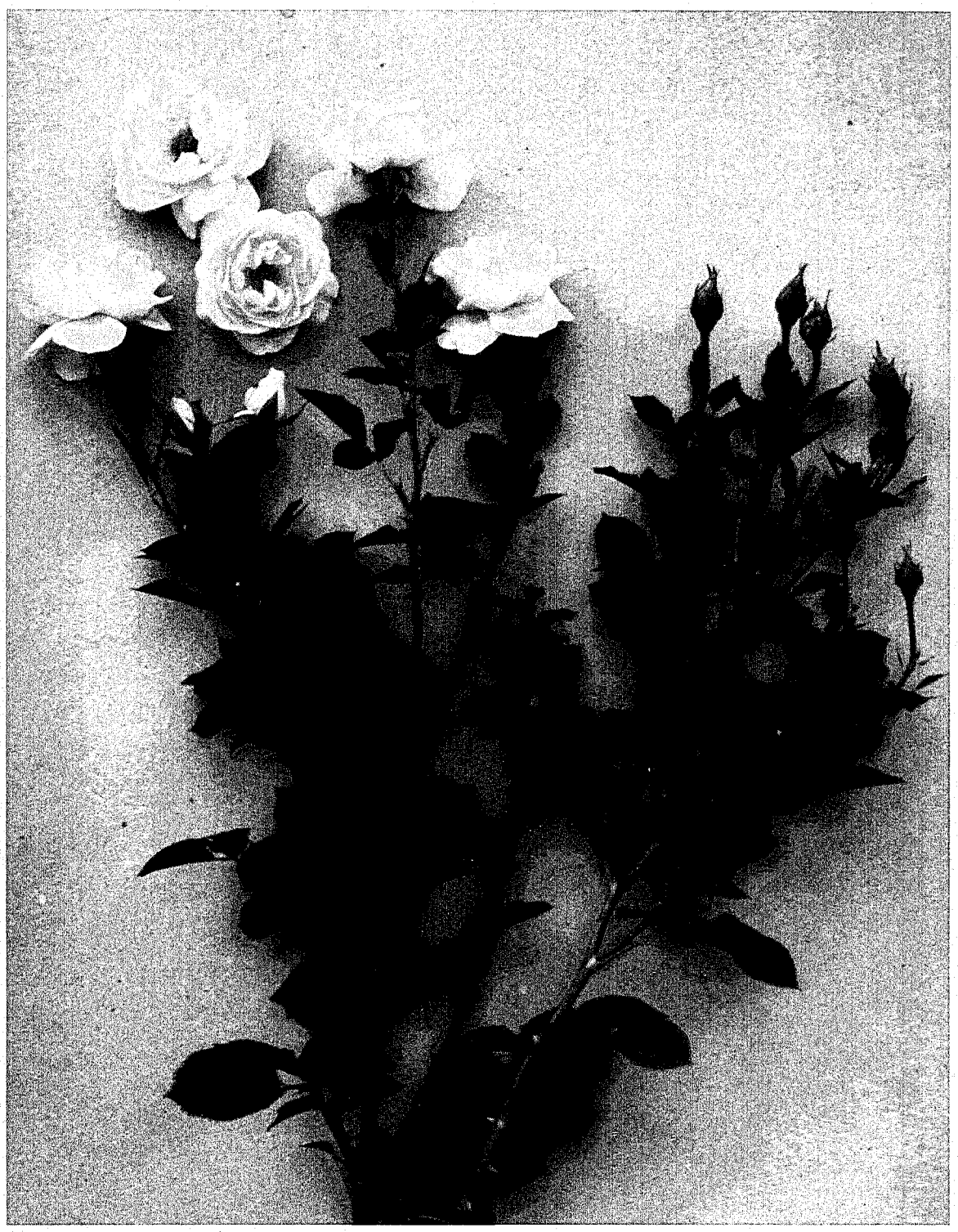

* * * * *